US006309889B1

(12) United States Patent
Cutler et al.

(10) Patent No.: US 6,309,889 B1
(45) Date of Patent: Oct. 30, 2001

(54) NANO-GRID MICRO REACTOR AND METHODS

(75) Inventors: Thomas A. Cutler, Los Altos Hills; Guy Lalonde, Woodside; Andrew J. G. Kelly, Palo Alto; Christopher R. Wagstrom, Los Altos, all of CA (US)

(73) Assignee: Glaxo Wellcome Inc., NC (US)

( * ) Notice: Subject to any disclaimer, the term of this patent is extended or adjusted under 35 U.S.C. 154(b) by 0 days.

(21) Appl. No.: 09/470,689

(22) Filed: Dec. 23, 1999

(51) Int. Cl.[7] ............................... C12Q 1/02; C12M 1/34
(52) U.S. Cl. ................. 436/165; 436/172; 422/102; 422/104; 435/4; 435/29; 435/33; 435/288.4; 435/288.7; 435/297.5
(58) Field of Search ................... 435/4, 7.92–7.95, 435/30, 33, 288.4, 288.7, 297.5, 305.2, 305.3, 308.1; 250/328; 356/246; 359/398; 422/102, 104; 436/519, 523, 43, 172, 164, 169, 46, 165

(56) References Cited

U.S. PATENT DOCUMENTS

| | | |
|---|---|---|
| 4,766,075 | 8/1988 | Goeddel et al. . |
| 5,382,513 | 1/1995 | Lam et al. . |
| 5,401,629 | 3/1995 | Harpold et al. . |
| 5,424,213 * | 6/1995 | Mougin . |
| 5,436,128 | 7/1995 | Harpold et al. . |
| 5,503,805 | 4/1996 | Sugarman et al. . |
| 5,506,141 * | 4/1996 | Weinreb et al. . |
| 5,565,324 | 10/1996 | Still et al. . |
| 5,604,130 * | 2/1997 | Warner et al. . |
| 5,635,598 | 6/1997 | Lebl et al. . |

(List continued on next page.)

FOREIGN PATENT DOCUMENTS

| | | |
|---|---|---|
| 0 516 443 A1 | 12/1992 | (EP) . |
| WO 94/19461 | 9/1994 | (WO) . |
| WO 96/24061 | 8/1996 | (WO) . |
| WO 96/30392 | 10/1996 | (WO) . |
| WO 97/37220 | 10/1997 | (WO) . |
| WO 98/25146 | 6/1998 | (WO) . |

OTHER PUBLICATIONS

Barrett and Goldstein (1985), "A Monoclonal Antibody Specific for a Dynorphin Precursor," Neuropeptides 6:113–120.
Barrett et al. (1992), "Selective Enrichment and Characterization of High Affinity Ligands from Collections of Random Peptides on Filamentous Phage," Anal. Biochem. 204:357–364.
Bazan et al. (1994), "Platelet–activating Factor and Retinoic Acid Synergistically Activate the Inducible Prostaglandin Synthase Gene," Proc. Natl. Acad. Sci. USA 91:5252–5256.
Berke (1995), "The CTL's Kiss of Death," Cell 81:9–12.
Chen et al. (1995), "Tethered ligand library for discovery of peptide agonists," J. Biol. Chem. 270:23398–23401.
Cull et al. (1992), "Screening for Receptor Ligands Using Large Libraries of Peptides Linked to the C terminus of the lac Repressor," 89:1865–1869.

(List continued on next page.)

Primary Examiner—William H. Beisner
(74) Attorney, Agent, or Firm—Townsend and Townsend and Crew LLP

(57) ABSTRACT

The invention provides exemplary devices and methods to facilitate the performance of assays. In one embodiment, one such device comprises a holding member having a top surface, a bottom surface, and a plurality of holding locations that are adapted to hold at least one article, such as a solid support and/or a cell. When within the holding locations, the articles are preferably disposed below the top surface. A membrane is positioned above the top surface of the holding member, and a pressure system is provided to apply positive pressure to the membrane to force the membrane against the top surface of the holding member. In this way, a seal may be provided between the holding locations.

44 Claims, 8 Drawing Sheets

U.S. PATENT DOCUMENTS

| | | |
|---|---|---|
| 5,681,741 * | 10/1997 | Atwood et al. . |
| 5,708,153 | 1/1998 | Dower et al. . |
| 5,747,334 | 5/1998 | Kay et al. . |
| 5,789,184 | 8/1998 | Fowlkes et al. . |
| 5,851,492 * | 12/1998 | Blattner . |
| 5,958,703 | 9/1999 | Dower et al. . |
| 6,027,695 * | 2/2000 | Oldenburg et al. . |

OTHER PUBLICATIONS

Felder et al. (1996), "A new combination of protecting groups and links for encoded synthetic libraries suited for consecutive tests on the solid phase and in solution," Molecular Diversity 1(2):109–112.

Frank (1993), "Strategies and techniques in simultaneous solid phase synthesis based on the segmentation of membrane type supports," Bioorganic & Medicinal Chemistry Letters 3(3):425–430.

Gossen and Bujard (1992), "Tight Control of Gene Expression in Mammalian Cells by Tetracycline–responsive Promoters," Proc. Natl. Acad. Sci. USA 89:5547–5551.

Himmler et al. (1993), "Functional Testing of Human Dopamine $D_1$ and $D_5$ Receptors Expressed in Stable cAMP–responsive Luciferase Reporter Cell lines," J. Receptor Res. 13(1–4):79–94.

Kinsella et al. (1991), "Molecular Cloning and Characterization of a Candida tsukubaensis α–Glucosidase Gene in the Yeast Saccharomyces cerevisiae," Curr. Genet. 20:45–52.

Kumar et al. (1992), "Saccharomyces cerevisiae Cells Secreting an Aspergillus Niger β–galactosidase Grown on Whey Permeate," Biotech. 10:82–85.

Martens et al. (1995), "Peptides Which Bind to E–selectin and Block Neutrophil Adhesion," J. Biol. Chem. 270:21129–21136.

Miller (1972), "Experiment 33, Penicillin and Ampicillin Treatment for the Isolation of Auxotrophic Mutants," in Experiments in Molecular Genetics, Cold Spring Harbor Laboratory 33:230–234.

Moreira et al. (1992), "Evaluation of Reporter Genes in Mammalian Cell Lines," Methods in Molecular and Cellular Biology 3:23–29.

Needels et al. (1993), "Generation and screening of an oligonucleotide–encoded synthetic peptide library," Proc. Natl. Acad. Sci. USA 90:1007–10704.

Normie (1996), "System Uses Photonics for Early Tumor Detection," Biophotonics News, Sep./Oct., pp. 24–25.

Paravicini et al. (1992), "The Osmotic Integrity of the Yeast Cell Requires a Functional PKC1 Gene Product," Mol. Cell Biol. 12:4896–4905.

Price et al. (1995), "Functional Coupling of a Mammalian Somatostatin Receptor to the Yeast Pheromone Response Pathway," Mol. Cell. Biol. 15:6188–6195.

Schatz (1993), "Use of Peptide Libraries to Map the Substrate Specificity of a Peptide–Modifying Enzyme: A 13 Residue Consensus Peptide Specifies Biotinylation in Escherichia coli," Biotech. 11:1138–1143.

Schneider et al. (1996), "An In Vitro Assay of β–Galactosidase from Yeast," BioTechniques 20:960–962.

Smith et al. (1995), "Rapid identification of highly active and selective substrates for stromelysin and matrilysin using bacteriophage peptide display libraries," J. Biol. Chem. 270:6440–6449.

Vallette et al. (1995), "Unsaturated Fatty Acids Synergistically Enhance Glucocorticoid–induced Gene Expression," Cellular Signalling 7:319–323.

Whitehorn et al. (1995), "A Generic Method for Expression and Use of "Tagged" Soluble Versions of Cell Surface Receptors," Bio/Technology 13:1215–1218.

Wrighton (1991), "Use of Tissue–Plasminogen Activator as a Reporter Gene," Chapter 16 of Methods in Molecular Biology, vol. 7: Gene Transfer and Expression Protocols, E.J. Murray, ed., The Humana Press Inc., Clifton, NJ, pp. 209–215.

Yamauchi et al. (1993), "Phosphatidylinositol 3–Kinase Functions Upstream of Ras and Raf in Mediating Insulin Stimulation of c–fos Transcription," J. Biol. Chem. 268:14597–14600.

Zaworski and Gill (1990), Use of Saccharomyces cerevisiae Expressing β–Galactosidase to Screen for Antimycotic Agents Directed against Yeast Cell Wall Biosynthesis and Possible Application to Pathogenic Fungi, in Molecular Biology Research, Upjohn Company, Kalamazoo, Michigan, 34:660–662.

Zuckermann et al. (1994), "Discovery of Nanomolar Ligands for 7–Transmembrane G–Protein Coupled Receptors from a Diverse N–(Substituted)glycine Peptoid Library," J. Med. Chem. 37:2678–2685.

Clontech Product Report, "Reporter Assays & Vectors 26," pp. 161–164, (No Date Provided).

Corning Product Report, "Fotoform®: a material and a capability.", (No Date Provided).

Pharmacia Biotech Product Report, "Instructions Cytodex®1, Cytodex 2, Cytodex 3.", (1994).

Tropix Product Report, "Phospha–Light™.", (1996).

* cited by examiner

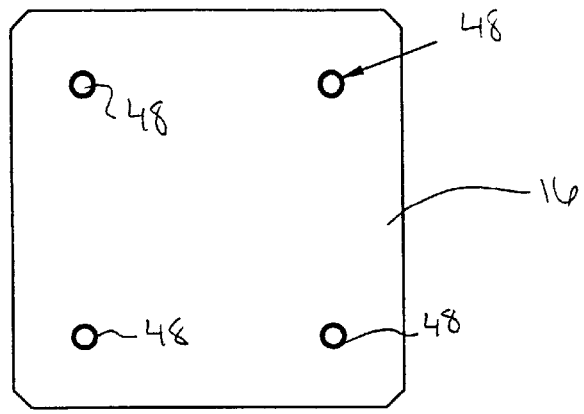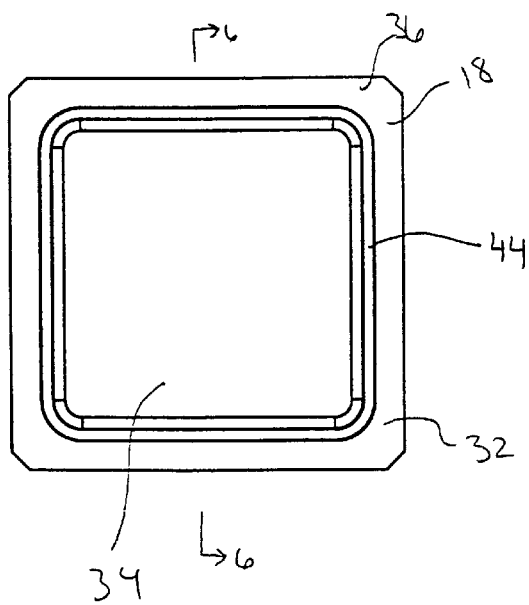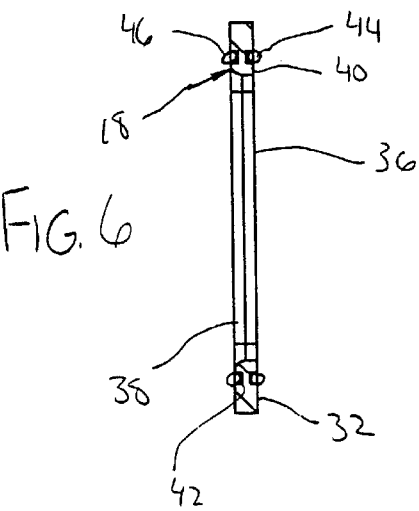

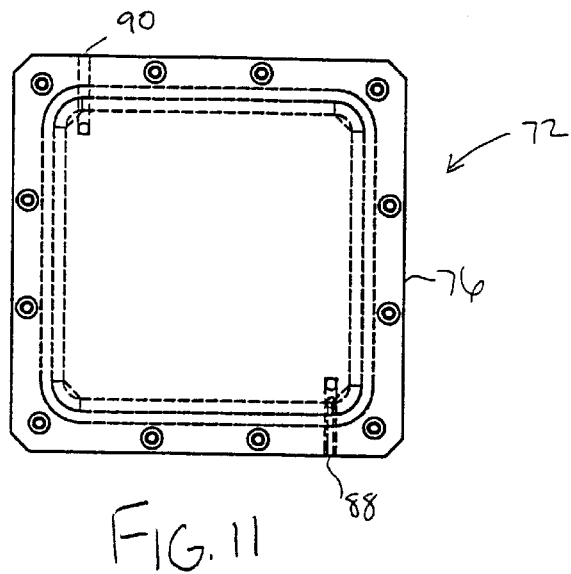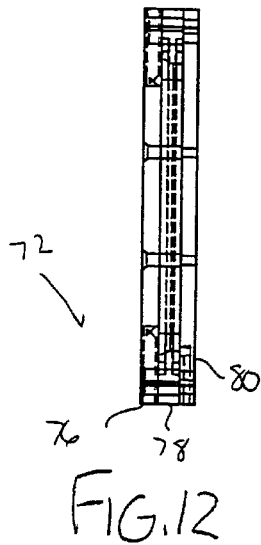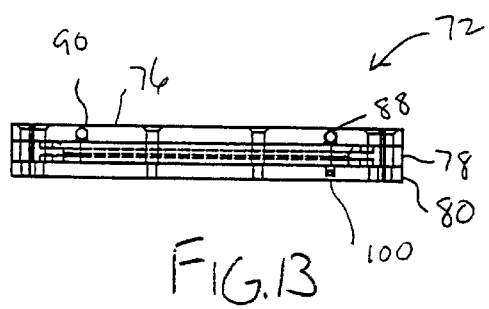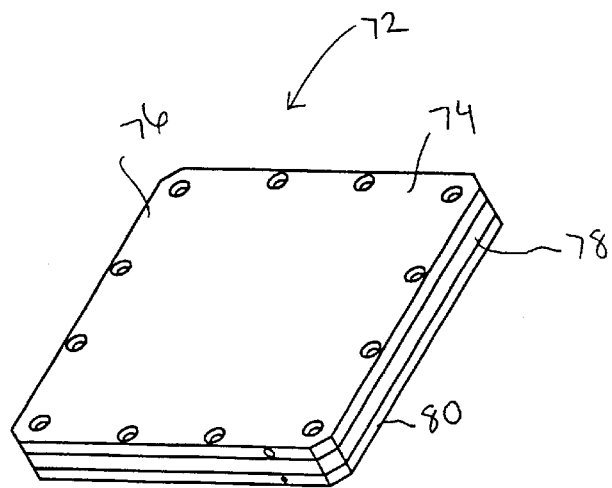
FIG. 11
FIG. 12
FIG. 13
FIG. 10

NANO-GRID MICRO REACTOR AND METHODS

BACKGROUND OF THE INVENTION

This invention relates generally to the field of assays, and in particular to techniques to facilitate the performance of such assays in a high throughput manner. In one particular aspect, the invention relates to the organization of solid supports and/or organisms, such as cells, that are used in performing such assays.

The creation of large chemical libraries has led to the use of a wide variety of assays to evaluate such libraries. As is known in the art, such chemical libraries may be created using a variety of synthesizing techniques, such as those described in U.S. Pat. Nos. 5,503,805 and 5,708,153, the complete disclosures of which are herein incorporated by reference. Typically, such synthesizing processes utilize solid supports, such as small resin beads, onto which the chemicals are synthesized.

Because of the immense size of such libraries, it is desirable to find ways to evaluate the chemicals in a high throughput manner. However, this can be difficult due to the nature of many existing assay formats. For example, some assays involve the use of living mammalian cells or other organisms. This can be especially challenging because of the difficulty in handling and/or organizing the solid supports and the cells, as well as because of the need to provide nutrients to keep the cells viable.

Merely by way of example, one type of assay is a cell reporter assay utilizing cells that produce a signal upon activation of a receptor. Hence, if a chemical that is released from a solid support activates the receptor, a signal is produced. Standard detectors may then used to detect the signal. With such assays, the ability to screen large numbers of reactions while also maintaining cell viability can be especially challenging.

Another type of assay is a "bead marking" assay where libraries of compounds are released from beads and permitted to diffuse to inducible cells where they interact with target receptors and induce the cells to produce and secrete an enzyme. The enzyme diffuses back to the beads and "marks" them by metabolizing a substrate covalently attached to the beads. Such an assay is described generally in copending U.S. patent application Ser. No. 08/758,307, filed Mar. 12, 1996, now U.S. Pat. No. 5,958,703, the complete disclosure of which is herein incorporated by reference.

To enhance such an assay as a drug discovery tool, it would be desirable to minimize the number of falsely marked beads. For example, a bead can be falsely marked if it comes into physical contact with a cell. Another way is if a cell that was induced by a compound from a positive bead marks a bead with an inactive compound through excessive diffusion of a compound or enzyme.

Another group of assays that can pose challenges when utilized in a high throughput manner are competition assays that are based on the interference of the binding of two ligands. High throughput screening of such assays while maintaining cell viability can be difficult.

Hence, the invention is related to techniques to facilitate the performance of various assays that utilize solid supports and/or other organisms, such as cells, in an efficient manner. In this way, the invention provides for the screening of large chemical libraries in a high throughput manner using a wide assortment of assay formats.

SUMMARY OF THE INVENTION

The invention provides exemplary devices and methods to facilitate the performance of assays. In one embodiment, one such device comprises a holding member having a top surface, a bottom surface, and a plurality of holding locations that are adapted to hold one or more articles, such as one or more solid supports and/or cells. When within the holding locations, the articles are preferably disposed below the top surface. A membrane is positioned above the top surface of the holding member, and a pressure system is provided to apply positive pressure to the membrane to force the membrane against the top surface of the holding member. In this way, a seal may be provided between the holding locations, with the membrane being spaced apart from the articles.

In one aspect, the pressure system comprises a housing that defines a chamber sized to receive the holding member and the membrane. The housing has an inlet port to permit a fluid, such as a gas or a liquid, to be supplied into the chamber to force the membrane against the top surface of the holding member. In another aspect, the housing may further include an outlet port to permit fluids to be evacuated from the chamber.

In one particular aspect, the housing further comprises an upper window, a lower window, and a spacer between the upper window and the lower window. Further, the inlet port extends through the upper window, and the holding member is configured to fit within the spacer. With such a configuration, the membrane may be coupled to the top window so as to be spaced apart from the holding member until operation of the pressure system to force the membrane against the top surface. In this way, the holding member may be loaded with solid supports and then placed onto the lower window while being framed by the spacer. The upper window may then be placed onto the spacer, with the membrane being spaced apart from the holding member.

Conveniently, seals may be positioned between the upper window and the spacer and the lower window and the spacer. Also, a vent may be formed within the lower window. In one particular aspect, an upper frame may be disposed above the upper window and a lower frame may be disposed below the lower window. Further, at least one securing mechanism may be provided to secure the upper frame to the lower frame.

In one aspect, the upper and lower windows may be constructed of an acrylic plastic that permits the transmission of ultraviolet light down to at least 270 nm. In this way, chemicals on the solid supports may be released by ultraviolet photolysis while disposed within the device.

In yet another aspect, the holding mechanism comprises a plate, and the holding locations comprise an array of wells formed in the plate. Conveniently, the wells may define a volume in the range from about 0.1 nl to about 100 nl, and more preferably from about 1 nl to about 25 nl. In still another aspect, an organism is coupled to the membrane. For example, the organism may comprise mammalian cells, insect cells, plant cells, bacteria, yeast and the like. In another aspect, the membrane is selectively permeable, e.g., based on molecular weight. In this way, nutrients and gases may be provided to the organisms while the membrane is forced against the plate.

In another embodiment, the housing comprises an upper window having the inlet port and an outlet port, a spacer that is adapted to receive the holding member, and a lower plate having a vent. Conveniently, at least one clamping device may be provided to clamp the spacer between the upper window and the lower plate. In one aspect, the housing may have a thickness that is less than about 1.5 cm to permit the device to be used with a fluorescence or a luminescence microscope. However, it will be appreciated that the devices may be constructed to be larger depending on the objective lens of the microscope.

The invention further provides an exemplary method for organizing items, such as solid supports, cells and the like. According to the method, items that each have at least one associated chemical or biological component (such as a cell that is configured to produce and secrete an enzyme) are placed into a plurality of holding locations within a holding member such that the items are disposed below a top surface of the holding member. A membrane is then forced onto the top surface of the holding member to cover the holding locations and to provide seal between the holding locations. In this way, the membrane is kept spaced apart from the items while still providing a seal to prevent or reduce the chances of cross contamination between the holding locations.

Depending on the nature of the assay to be performed, each holding location may receive a single item or multiple items. For example, each holding location may receive a single solid support, such as a bead, multiple solid supports, a single cell, multiple cells, or combinations thereof. In one step of the method, a liquid is placed within the holding locations prior to forcing the membrane against the holding member to provide a moist environment and to supply nutrients to each holding location. In this way, nutrients may be provided to any cells or other organisms within the holding locations. In one particular aspect, an organism is placed on the underside of the membrane such that the organism is positioned above each holding location when the membrane is forced onto the holding member. Exemplary organisms that may be used include mammalian cells, insect cells, plant cells, bacteria, and yeast. Conveniently, the fluid within the holding locations may provide nutrients to such organisms. Further, the membrane may be fluid permeable so that other nutrients may be provided to the holding locations through the membrane, e.g. using the same fluid to hold the membrane to the holding member.

The invention further provides an exemplary method for performing assays. According to the method, solid supports and/or cells are placed into a plurality of holding locations within a holding member such that the solid supports and/or cells are disposed below a top surface of the holding member. The solid supports may include one or more synthesized chemicals. A substrate, such as a caged fluorescent substrate, may also be included in the holding locations. The substrate is uncaged by an enzyme produced upon cell activation. A membrane is forced onto the top surface of the holding member to cover the holding locations and to provide seal between the holding locations. Any chemical or biological reactions occurring within the holding locations are then evaluated.

In one aspect, at least a portion of the chemicals may be released from the solid supports. Any interactions between the released chemicals and a cell or other organism may then be evaluated. For example, the released chemical may be used as part of a bead marking assay or a cell reporter assay. In another aspect, an organism may be provided on the membrane to interact with the released chemical. Examples of organisms that may be coupled to the membrane include mammalian cells, insect cells, plant cells, bacteria, yeast, and the like.

As one specific example of a bead marking assay, the organism may comprise a layer of cells placed onto an underside of the membrane such that each holding location receives at least some of the cells when the membrane is forced onto the top surface. Further, each holding location may receive a solid support that includes a substrate covalently attached thereto. In this way, the released chemicals may diffuse to any inducible cells on the membrane to interact with a target receptor and induce the cells to produce and secrete an enzyme that diffuses back to the associated solid support and metabolizes the substrate to mark the solid support.

As one specific example of a cell reporter assay, the holding member may contain a caged dye and a cell expressing a receptor such that if the released chemical binds with the receptor, the dye is activated. Conveniently, the cell may be placed within the holding location rather than on the membrane. With such an assay, the holding locations may be scanned with an optical sensor, such as a fluorescence or luminescence detector, to detect a signal, such as an activated dye.

In one aspect, the membrane is permeable so that when a pressurized fluid is introduced against the membrane, nutrients may permeate to feed the cells. In another aspect, a liquid is placed into each holding location prior to forcing the membrane onto the holding member. For example, the placing step may comprise introducing a slurry of solid supports onto the holding member and scraping the slurry across the holding member.

In another aspect, the holding mechanism comprises a plate having a top surface, and the holding locations comprise wells in the plate. In this way, a pressurized fluid may be introduced against the membrane to force the membrane against the top surface. In one aspect, the fluid is pressurized to a pressure in the range from about 2 psi to about 5 psi. In another aspect, the fluid is selected from a group of fluids consisting of gases, such as air, $CO_2$, $O_2$, nitrogen, and combinations thereof, and liquids, such as water, buffer solutions and the like. In yet another aspect, the membrane may be constructed from membranes such as gas permeable membranes, such as silicone rubber membranes, polyurethane membranes, polyethylene membranes, polypropylene membranes, perfluoro polymer membranes, composite membranes, and dialysis membranes, such as cellulose acetate membranes, and the like.

In one particular aspect, the solid supports are placed beneath ultraviolet light to photo release the chemicals. In another aspect, the solid supports are removed from the holding locations following marking of the solid supports.

BRIEF DESCRIPTION OF THE DRAWINGS

FIG. 4 is a top view of an upper window of the device of FIG. 1.

FIG. 5 is a top view of a spacer of the device of FIG. 1.

FIG. 6 is a cross sectional side view of the spacer of FIG. 5.

FIG. 10 is a top perspective view of an alternative embodiment of a device to facilitate the performance of assays according to the invention.

FIG. 11 is a top view of the device of FIG. 10 with the internal components being shown in phantom line.

FIG. 12 is a right side view of the device of FIG. 11.

FIG. 13 is a front view of the device of FIG. 11.

DESCRIPTION OF THE SPECIFIC EMBODIMENTS

Figure 1:
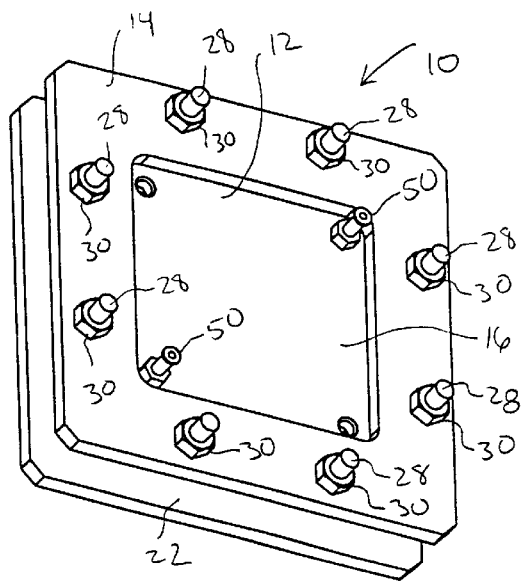
FIG. 1 is a top perspective view of a device to facilitate the performance of assays according to the invention.

The invention provides for the organization of items, such as solid supports, including beads, organisms, such as mammalian cells, insect cells, plant cells, bacteria, yeast, and the like to facilitate the performance of assays in a high throughput manner. When utilizing solid supports, the invention also provides techniques for releasing chemicals from the solid supports to facilitate their evaluation. If the assays involve the use of organisms, such as cells, the invention further provides techniques for maintaining the viability of the cells, e.g. by providing proper nutrients to the cells.

The invention may utilize a holding member having a plurality of holding locations to hold the solid supports and/or organisms. The holding member may be configured such that the solid supports and/or organisms are spaced apart from each other when within the holding locations. In some embodiments, the solid supports may also be held within the holding locations such that the solid supports are disposed below a top surface of the holding member. As one example, the holding member may comprise a plate having an array of wells. The wells may be arranged in any type of format, including both unconventional and standard formats, such as 96 well formats, 864 well formats, 1536 well formats, and the like. To improve the throughput, it may be desirable to increase the density of wells so that the plate includes high numbers of wells within a given location. As such, the wells may be constructed to hold relatively small volumes, including volumes in the range from about 0.1 nl to about 100 nl, and more preferably from about 1 nl to about 25 nl. Examples of other holding members that may be employed include porous membranes having recessed regions, plates with through holes, and the like.

The items may be placed into the holding locations in a variety of ways. For example, when the holding locations comprise wells, the items may be placed into a slurry that is poured over a top surface of the plate. The slurry may then be scraped over the plate with a flat surface to force the items (along with an amount of the slurry) into the wells and to scrape any excess from the plate. As another alternative, the holding member may be porous or include through holes so that suction may be supplied to suction solid supports into each holding location. As still another example, solid supports or cells may be attached to a membrane, which is then positioned below a plate having a plurality of through holes.

Depending on the particular assay, each holding location may be configured to receive a wide assortment of items. For example, each holding location may receive only a single solid support or multiple solid supports. As another example, each holding location may receive an organism, such as a cell, alone or in combination with one or more other organisms and/or solid supports.

The invention also utilizes a membrane that is forced onto a top surface of the holding member after the items have been placed into the holding locations. The membrane may provide a variety of functions. For example, the membrane may provide a seal about each holding location so that cross contamination is prevented between the holding locations. As another example, the membrane may serve as a support onto which a variety of organisms may be coupled. In this way, when the membrane is forced onto the holding member, the organisms are placed above each holding location, typically being spaced apart from any solid support or cell that is disposed within the holding location. Examples of organisms that may be coupled to the membrane include mammalian cells, insect cells, plant cells, bacteria, yeast, and the like. A further function of the membrane may be to permit the diffusion of nutrients to the organisms that are within the holding locations. For example, the membrane may be permeable to certain nutrients to permit such nutrients to permeate the membrane so that they will be supplied to the organisms. Conveniently, such nutrients may be included in the same fluids employed to hold the membrane against the holding member as described hereinafter. Another function of the membrane is to facilitate imaging of the holding locations or wells by ensuring that liquid exists within the holding locations. Use of the membrane also provides a way to buffer the pH of the fluid in the wells. Examples of membranes that may be employed include gas permeable membranes, such as those sold under the trade name of Pharmelast, including, for example, silicone rubber membranes, polyurethane membranes, polyethylene membranes, polypropylene membranes, perfluoro polymer membranes, composite membranes, and dialysis membranes, such as cellulose acetate membranes, and the like.

To force the membrane onto the top surface of the holding member, a variety of pressure systems may be employed. As one example, a pressurized fluid may be introduced against a top surface of the membrane to force a bottom surface of the membrane (which may optionally include an attached organism) against the top surface of the holding member. The pressurized fluid holds the membrane against the top surface and provides a seal between the holding locations. In one aspect, the membrane is configured to seal against the holding member beginning at a middle portion of the holding member and then in an outward manner. In this way, liquids displaced from the holding locations are forced outward and then removed from the top surface. Conveniently, a spacer may be employed to keep the membrane spaced apart from the holding member until application of the fluid to permit the membrane to adhere to the holding member in such a manner. Examples of fluids that may be used to force the membrane against the top surface include gases, such as air, $CO_2$, $O_2$, nitrogen, and combinations thereof, and liquids, such as water, buffer solutions, tissue culture media and the like. Since the membrane may be configured to be permeable, nutrients may diffuse through the membrane to provide nutrients to any organisms on the underside of the membrane.

Other ways to force the membrane onto the top surface include the use of mechanical forces. For instance, a bowed surface may be forced onto the membrane to force the membrane onto the top surface in an inward to outward manner. In one aspect, the forces may tension the membrane against the top surface in a flat or curved configuration.

The invention facilitates the performance of a wide variety of assays in a high throughput manner. For example, the invention may be used in connection with a cell reporter type assay. With such an assay, the holding locations may receive solid supports and cells, and have a caged fluorescent substrate. The cells may be on the membrane or sedimented within the holding locations Chemicals are released from the solid supports to permit the chemicals to come into contact with the cells. If a cell is stimulated, an enzyme is produced that clips a protecting group on the substrate to permit the substrate to become fluorescent. A fluorescent microscope may then be employed to scan the holding locations.

As another example, the invention may be used in connection with bead marking assays as described generally in copending U.S. patent application Ser. No. 08/758,307, previously incorporated by reference. With such assays, each holding location may receive one or more solid supports that each include a substrate covalently attached thereto. Further, the membrane may include a layer of mammalian cells, such as CHO or HEPG2. In this way, the chemicals on the solid supports may be released and permitted to diffuse to the cells on the membrane. The chemicals may then interact with a target receptor and induce the cells to produce and secrete an enzyme that diffuses back to the associated solid support and metabolizes the substrate to mark the solid support. The solid supports may then be removed from the holding locations and scanned with a detector, such as a fluorescence activated cell sorter (FACS) machine, commercially available from a variety of suppliers, such as Becton Dickinson. In some cases, the solid supports may remain within the holding locations and scanned with a fluorescence microscope, a luminescence imager, or the like.

Another type of assay that may be used include reporter assays where released chemicals may react with a cell to produce an enzyme that causes, for instance, light to be emitted. Conveniently, the cells may be provided on the membrane or included within the holding locations. Other types of assays that may be used include competition assays, inhibition assays, bacterial assays, and the like.

Figure 2:
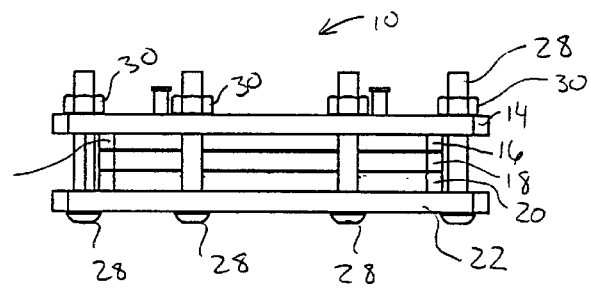
FIG. 2 is a side view of the device of FIG. 1.
Figure 3:
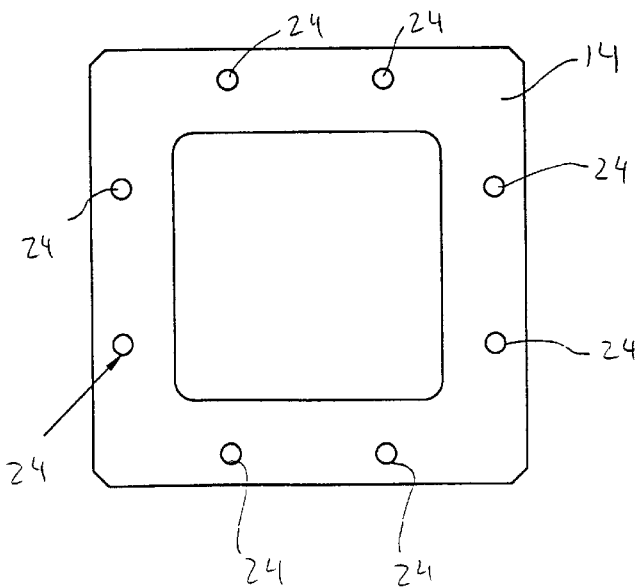
FIG. 3 is a top view of an upper frame of the device of FIG. 1.
Figure 8:
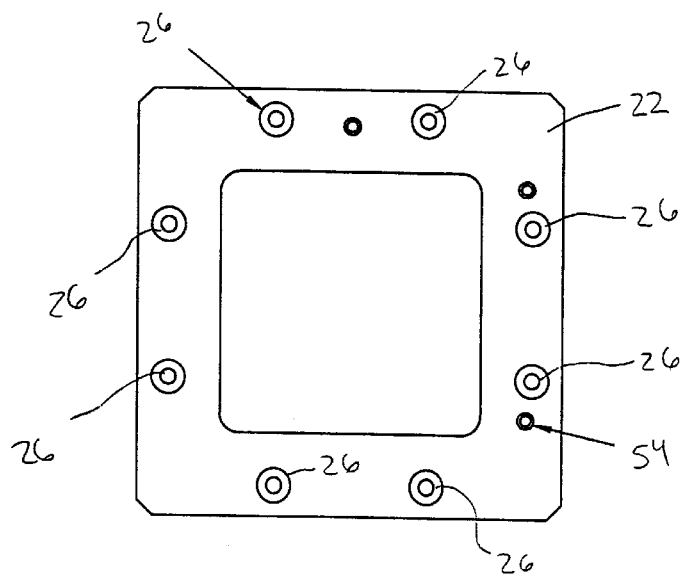
FIG. 8 is a bottom view of a lower frame of the device of FIG. 1.

Referring now to FIG. 1, one embodiment of a device 10 that may be employed to facilitate the performance of an assay will be described. As also shown in FIG. 2, device 10 comprises a housing 12 that is constructed of an upper frame 14, an upper window 16, a spacer 18, a lower window 20 and a lower frame 22. Each of these complements are stacked on top of each other as illustrated in FIG. 2. As best shown in FIGS. 3 and 8, upper frame 14 includes multiple holes 24 and lower frame 22 includes multiple holes 26. In this way, bolts 28 may be inserted through holes 24 and 26 and a nut 30 employed to force upper frame 16 toward lower frame 22 to sandwich upper window 16, spacer 18 and lower window 20 between frames 14 and 22.

Upper frame 14 and lower frame 22 are preferably constructed of a rigid material to permit nuts 30 to be torqued without significantly deforming the shape of frames 14 and 22. For example, materials that may be the frames include aluminum, stainless steel, and the like.

As best shown in FIGS. 5 and 6, spacer 18 comprises a frame 32 that has an outer periphery that is essentially the same as windows 16 and 20. Frame 32 further defines an open interior 34 to permit a cavity or chamber to be formed when device 10 is assembled. Interior 34 is sized so that it may receive a multi-well plate as described in greater detail hereinafter.

Frame 32 further includes an upper side 36 and a lower side 38. Upper side 36 includes a groove 40 while lower side 38 includes a groove 42. Disposed in groove 40 is an O-ring 44, and disposed in groove 42 is an O-ring 46. In this way, a seal is provided between upper windows 16 and spacer 18 and between lower window 20 and between spacer 18. In this manner, the cavity formed by interior 34 is sealed to prevent fluids from escaping between the interface with windows 16 and 20.

Referring now to FIG. 4, construction of upper window will be described. As shown, upper window 16 includes four holes 48. These holes extend through windows 16 to permit fluids to be either introduced into or withdrawn from the cavity formed by interior 34 (see FIG. 5). Although shown with four holes, it will be appreciated that other numbers of holes may be employed depending on the particular need. As shown in FIGS. 1 and 2, two of holes 48 are provided with connectors 50 which provide a convenient coupling mechanism to facilitate the introduction of fluids either into or from the device 10.

Upper window 16 may be constructed of a material which will facilitate the adherence of the membrane to the window. In this way, prior to assembly, a membrane may be laid onto upper windows 16. When device 10 is assembled, the membrane will be positioned above interior 34 (see FIG. 5) so that it will be spaced apart from a multi-well plate that is disposed within interior 34. Conveniently, window 16 (as well as window 20) may be constructed of a UV transparent acrylic plastic that may permit the transmission of ultraviolet light down to at least about 270 nm. In this way, device 10 may be placed under UV light to permit chemicals to be photo-released from solid supports using a photolysis process which typically occurs between 360 nm to about 365 nm, as described hereinafter.

Figure 7:
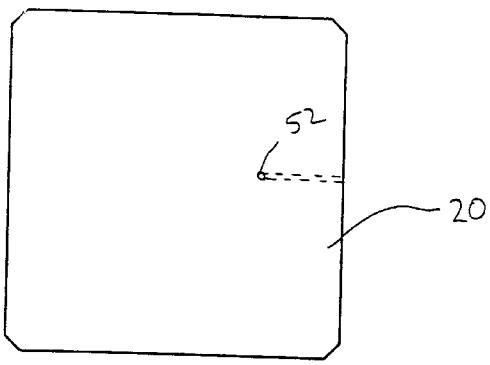
FIG. 7 is a top view of a lower window of the device of FIG. 1.

Referring to FIG. 7, lower window 20 will be described in greater detail. Conveniently, lower window 20 may be constructed to have the same size and the same material used to construct upper window 16. Lower window 20 may include a vent 52 that is employed to vent any excess fluids when pressure is supplied into the interior as described hereinafter.

Referring now to FIG. 8, lower frame 22 will be described in greater detail. Conveniently, frame 22 may be constructed to have the same dimensions as upper frame 14. Optionally, lower frame 22 may include alignment posts 54 to assist in proper positioning during assembly.

Figure 9:
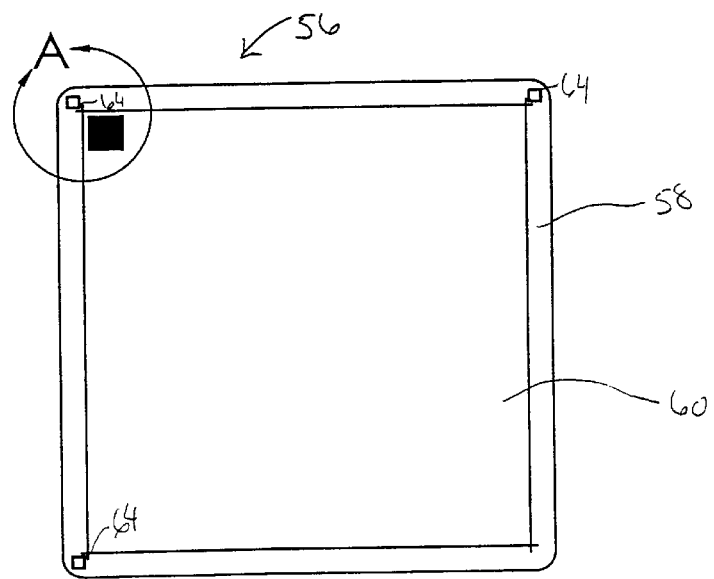
FIG. 9 is a top view of a plate having a plurality of wells that may be used with the device of FIG. 1 according to the invention.
Figure 9A:
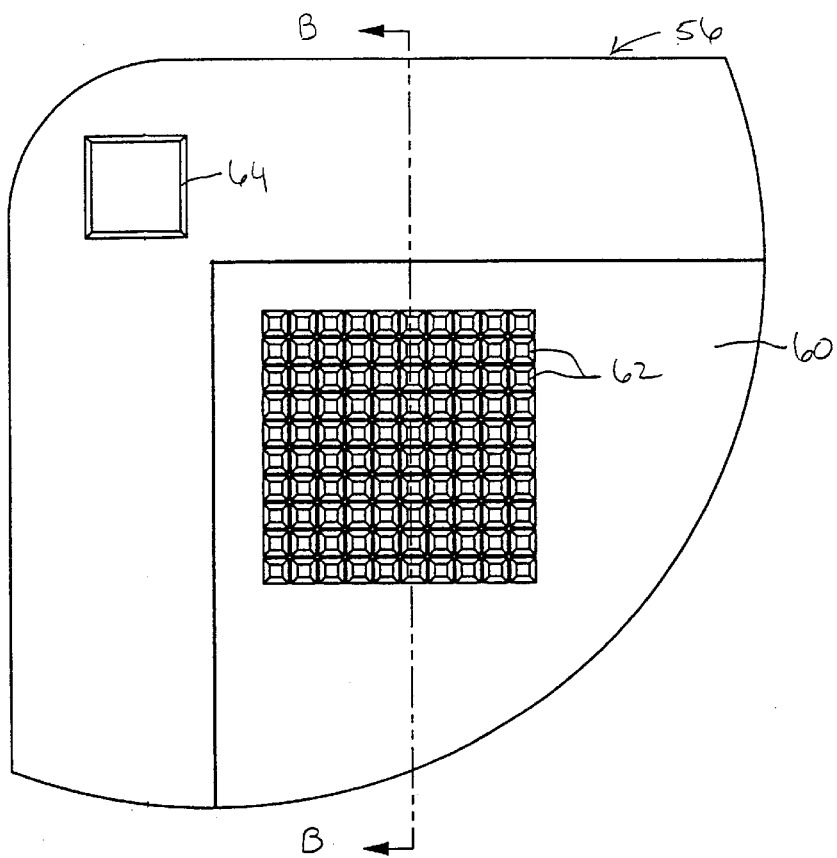
FIG. 9A is a more detailed view of a region A of the plate of FIG. 9.
Figure 9B:
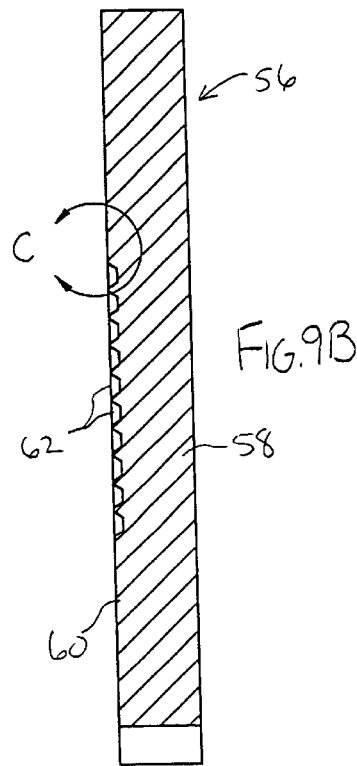
FIG. 9B is a cross sectional side view of the region FIG. 9A taken along lines B—B.
Figure 9C:
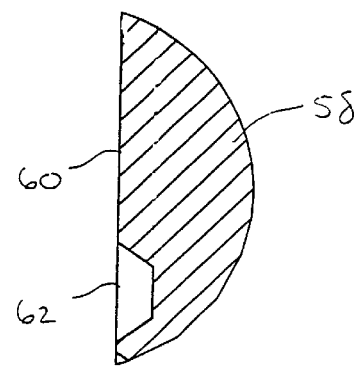
FIG. 9C is a more detailed view of a region C of the plate of FIG. 9B.

During assembly of device 10, a plate 56 is disposed within the interior 34 of frame 18 (see FIG. 5) as illustrated generally in FIGS. 9–9C. Plate 56 comprises a plate body 58 having a top surface 60 and an array wells 62 formed below top surface 60. For convenience of illustration, only a limited number of wells 62 are shown, it being appreciated that a major portion of top surface 60 will typically include wells identical to those illustrated. Merely by way of example, plate body 56 may have outer dimensions of about 8 cm by about 8 cm. Wells 62 may be about 10,000 to about 500,000 in number, although other numbers are possible. However, it will be appreciated that other numbers of wells having other volumes will be employed, depending on the particular application. One particular advantage of using such a high density of wells is that relatively large numbers of solid supports may be screened during a single process, thereby greatly increasing the throughput. Optionally, plate 56 may be provided with one or more registration marks 64 that serve as a locating device when scanning wells 62 with automated equipment as is known in the art.

To assemble device 10, lower window 20 is placed upon lower frame 22 so that vent hole 52 is facing upward. When upper window 20 is placed upon frame 22, window 20 is located within holes 26. Spacer 18 is then placed upon window 20 and plate 56 is placed within interior 34 so as to be resting upon lower window 20. Solid supports and/or cells will preferably already have been placed into wells 62 as described in greater detail hereinafter. The membrane is adhered to upper window 16, with any organisms on the membrane facing away from window 16. Window 16 is then placed onto spacer 18 such that the membrane (and any organisms) are facing wells 62. Preferably, plate 56 is configured to sit below the upper side 36 of spacer 18 so that the membrane on upper window 16 will be spaced apart from top surface 60 of plate body 58. Upper frame 14 may then be placed onto upper window 20 and bolts 28 and nuts 30 employed to secure the assembly together.

Figure 9D:
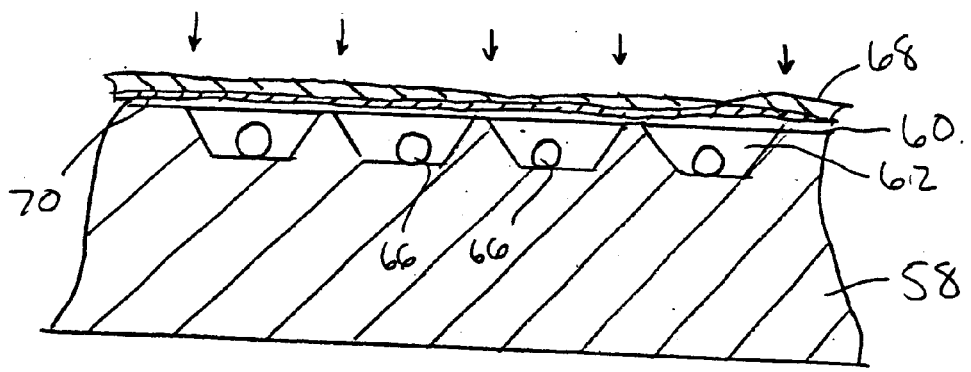
FIG. 9D illustrates the forcing of a membrane onto a section of the plate of FIG. 9B after beads have been plated into the wells according to the invention.

When assembled, a pressurized fluid may be introduced into any one of holes 48 (with the other holes being sealed) to force the membrane from upper window 16 and onto top surface 60 of plate body 58. Such a process is illustrated, for example, in FIG. 9D where plate 56 includes a plurality of solid supports 66 within wells 60. A membrane 68 is disposed above top surface 60 and has a layer of cells 70 coupled to membrane 68. As shown in FIG. 9D, the layer of cells 70 is spaced apart from top surface 60. As the pressurized fluid is introduced into device 10, membrane 68 is forced onto top surface 60 as illustrated by the arrows. In this way, some of the cells are disposed within each of wells 62 while remaining spaced apart from solid supports 66. Further, a seal is provided between each of wells 62 to prevent cross-contamination between the wells. Although not shown, solid supports 66 may be provided within a slurry so that each of wells 62 may also be filled with a liquid. When the pressurized fluid is applied, the center of the membrane 68 will typically first contact top surface 60. The rest of the membrane will then contact top surface 60 from inside to outside so that any excess liquid within wells 62 will be forced to the outer edges of plate body 56. Vent 52 in lower window 20 may be employed to vent any excess fluids.

Once the pressurized fluid is applied, the appropriate holes 48 may be closed so that the pressure may be maintained within the device to hold membrane 68 onto top surface 60. Conveniently, a stopcock, other valve, or the like may be employed to close holes 48.

One exemplary assay that may be performed with device 10 is a bead marking assay. Use of device 10 is particularly advantageous in that the solid supports within wells 62 may be physically separated from each other and placed into sealed wells so that the chances of falsely marking a bead will be greatly reduced. With such an assay, mammalian cells, such as CHO or HEPG2, may be grown in a monolayer onto a gas permeable sheet of a thin silicon rubber membrane, such a membrane sold under the trade name of Pharmelast. This monolayer of cells is pressed onto upper surface 60 when pressure is applied to device 10. Alternatively, the cells may be sedimented into each of the wells. Conveniently, a gas, such as air, oxygen, nitrogen, and the like, including various gas mixtures, may be introduced into one or more holes 48 to create a seal between individual wells 62 and membrane 68. The adherent nature of the cells keeps them stuck to membrane 68, physically separate from solid supports 66. Once the seal has been established, cross contamination between the wells is prevented. Device 10 may then be placed under UV light to allow solid supports 66 to be photolyzed in their wells 62, and the compounds that are released will be confined to those wells. If a compound induces a cell to produce a marking enzyme, that enzyme will be similarly confined, marking only positive beads. Cell viability is maintained by using a gas to force membranes 68 against plate body 58, i.e., membranes 68 will permit enough oxygen to pass through to maintain the cells as they mark the beads. Although shown with the monolayer of cells being attached to membrane 68, it will be appreciated that cells may be placed within individual wells 62.

Once a bead has been marked, it may be separated from the unmarked beads using a FACS machine, commercially available from Becton-Dickinson. Following photolysis, pressurized oxygen may once again be introduced in device 10 to refresh the cells. After the reactions have occurred, device 10 may be disassembled and plate 56 removed. Solid supports 66 may then be removed from the wells with ultrasound. The solid supports may then be stained to permit marked beads to be identified.

Figure 17:
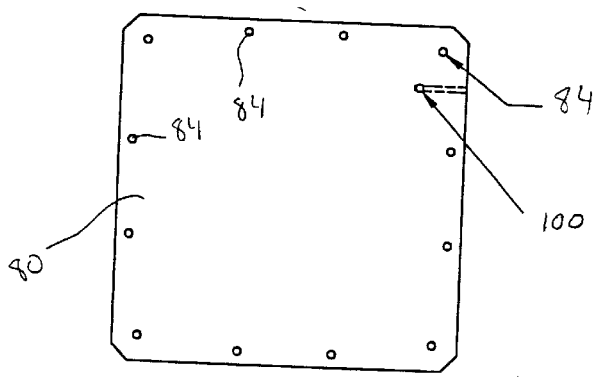
FIG. 17 is a top view of a lower plate of the device of FIG. 10.

Referring now to FIG. 10, an alternative embodiment of a device 72 will be described. Device 72 comprises a housing 74 that is constructed of an upper window 76, a spacer 78 and a lower plate 80. As also shown in FIGS. 11–14, upper window 76 includes a plurality of holes 82 to permit a bolt to be inserted through holes 82. As also shown in FIG. 17, lower plate 80 also includes a plurality of holes 84 to receive the bolts inserted through holes 82. Conveniently (as also shown in FIG. 15), spacer 78 includes holes 86 to also permit the bolts to passed through spacer 78. In this way, device 72 may be assembled by placing spacer 78 onto lower plate 80 and then placing upper window 76 onto spacer 78. Bolts are then inserted through holes 82–86 and secured in place to clamp the device together.

Figure 14:
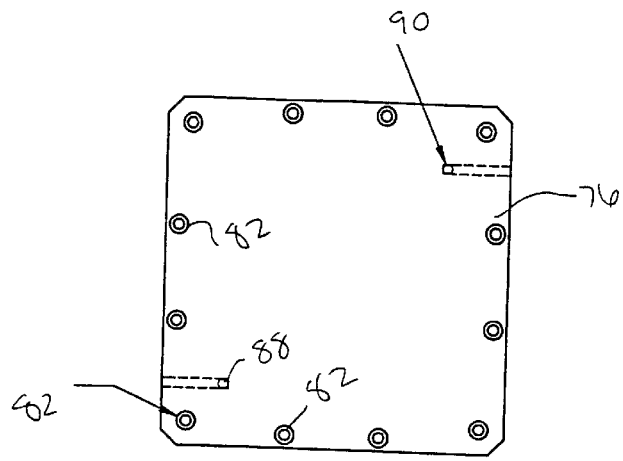
FIG. 14 is a top view of an upper window of the device of FIG. 10.
Figure 15:
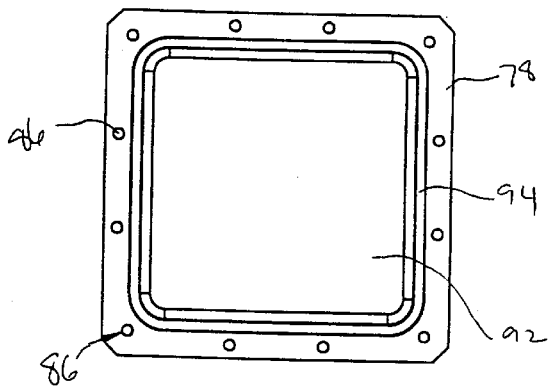
FIG. 15 is a top view of a spacer of the device of FIG. 10.
Figure 15A:
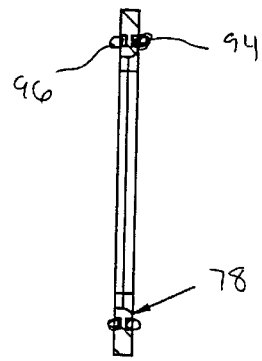
FIG. 15A is a cross sectional side view of the spacer of FIG. 15.

As best shown in FIGS. 11 and 14, upper window 76 includes an inlet 88 and an outlet 90. In this way, pressurized fluids may be introduced into and withdrawn from device 72.

Figure 16:
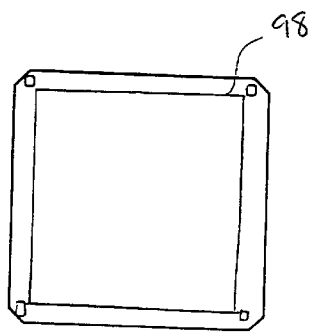
FIG. 16 is a top view of a multi-well plate of the device of FIG. 10.

Spacer 78 may be constructed to be similar to spacer 18 of the device 10 and defines an interior 92 that forms a chamber within device 72 when assembled. O-rings 94 and 96 are provided to create a seal between upper window 76 and lower plate 80 in a manner similar to that described in device 10. Interior 92 is sized to receive a multi-well plate 98 as illustrated in FIG. 16. Multi-well plate 98 includes a plurality of wells which are not illustrated due to their relatively small size. However, multi-well plate 98 may be constructed to be similar to plate 56 as previously described.

As also shown in FIG. 17, lower plate 80 includes a vent 100 to permit fluids to be vented from device 10.

Conveniently, lower plate 80 may be constructed of a generally rigid material so that the plate will not bow outward when pressure is introduced into device 70. Examples of materials that may be used to construct the plate include aluminum, stainless steel, and the like.

In use, the wells of plate 98 are filled with solid supports. Spacer 78 is positioned on lower plate 80 and plate 98 is placed into interior 94. Upper window 76 is then secured to lower plate 80 using bolts.

One particular feature of device 72 is its relatively compact size. For example, device 72 can include up to about 500,000 wells or more, while still having a height that is less than about 1.5 cm. In this way, device 72 may be used with various types of microscopes, without device 72 interfering with the objective of the microscope. Further, device 72 is particularly suited for receiving liquids to deflect the membrane to reduce the chances of reflection or refraction to enable a clearer view from the microscope. Conveniently, the inlet, outlet and vent holes are provided at the sides of device 72 so they also will not interfere with the microscope objective.

One particular assay with which device 72 may be employed is with a reporter type assay. With such an assay, cells are provided on a membrane or sedimented into the wells. The cells are preloaded with a caged fluorescent substrate. The membrane is then placed onto upper window 76 so that it is positioned above the wells when device 72 is assembled. A liquid, such as a buffer solution or water, is then introduced into device 72 through inlet 88 while outlet 90 is closed. The membrane is then forced onto plate 98 so that the cells are positioned above each of the wells (if the cells are provided on the membrane), with the membrane providing a seal between the wells similar to that described with other embodiments. The compounds are then released from the solid supports by photolysis or other releasing techniques. If a cell is stimulated, an enzyme is produced to uncage the substrate and to permit the substrate to become fluorescent. A fluorescence detector, such as a fluorescence microscope, may then be employed to detect the substrate. Conveniently, device 72 is constructed so that it may be placed on a conventional microscope stage and scanned in the X-Y fashion as is known in the art to detect the activated cells. Following this step, the plate may be removed from device 72 and the beads that are associated with wells producing a positive result may then be picked out, either manually, using a bead picking device or other automated equipment as is known in the art.

Figure 18:
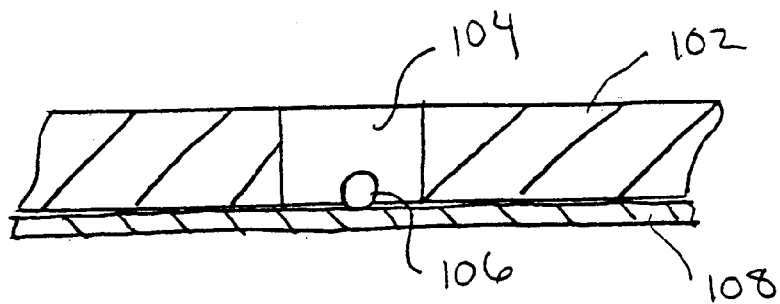
FIG. 18 is a cross sectional side view of a plate having a through hole for receiving a solid support that is coupled to a membrane according to the invention.
Figure 19:
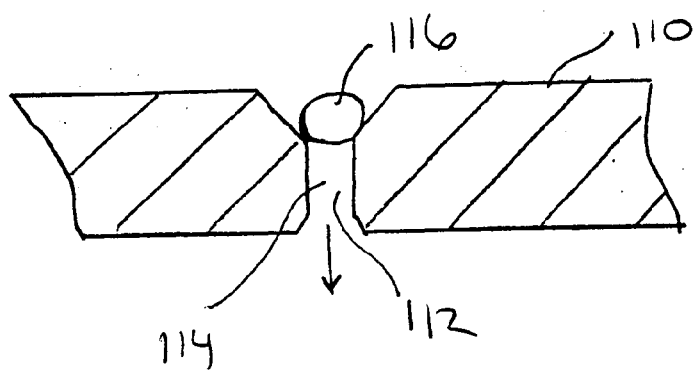
FIG. 19 is a cross sectional side view of a plate having a through hole through which a vacuum may be applied to attract a solid support according to the invention.
Figure 20:
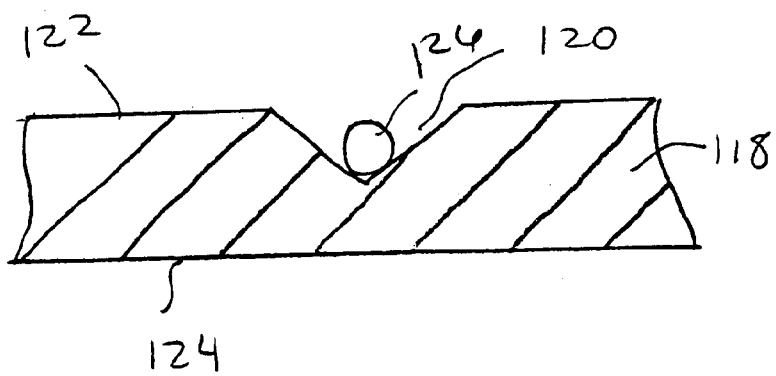
FIG. 20 is a cross sectional side view of a filter membrane that may be employed to attract solid supports according to the invention.

Referring now to FIGS. 18–20, alternative schemes for placing solid supports into holding locations of a holding member will be described. As shown in FIG. 18, a holding member 102 includes a plurality of through holes 104 (only one being shown for convenience of illustration). The through holes serve as holding locations for solid supports 106. To place solid supports 106 in through holes 104, the solid supports are arranged onto a membrane 108 having a sticky surface. The solid supports are arranged in an organized manner so that when holding member 102 is placed on top of membrane 108, solid supports 106 are disposed within through holes 104.

Shown in FIG. 19 is a holding member 110 having a plurality of through holes 112 (only one being shown for convenience of illustration). Through hole 112 includes a necked region 114 that has a cross-sectional dimension which is smaller than the diameter of a solid support 116. In this way, a vacuum may be applied to through hole 112 to suction a solid support 116 into through hole 112 until it engages net region 114.

Shown in FIG. 20 is a holding member 118 that includes multiple recessed regions 120 (only one being shown for convenience of illustration). Holding member 118 includes a top surface 122 and a bottom surface 124. The degree of filtration decreases from top surface 122 to bottom surface 124. In this way, the degree of filtration of holding member 118 at recessed regions 120 will be less than the rest of the filter media. In this way, when a vacuum is applied to bottom surface 124, a greater amount of vacuum will be created within recessed regions 120. In this way, solid supports 126 will be drawn into recessed regions 120.

The invention has now been described in detail for purposes of clarity of understanding. However, it will be appreciated that certain changes and modifications may be practiced within the scope of the appended claims.

What is claimed is:

1. A device to facilitate the performance of assays, the device comprising:
   a holding member having a top surface, a bottom surface, and a plurality of holding locations that are adapted to hold at least one article such that the articles are disposed below the top surface;
   a membrane positioned above the top surface of the holding member; and
   a pressure system to apply positive pressure to the membrane to force the membrane against the top surface of the holding member and provide a seal between the holding locations, wherein the pressure system comprises a housing that defines a chamber sized to receive and enclose the holding member and the membrane, the housing having an inlet port to permit a fluid to be supplied into the chamber to force the membrane against the top surface of the holding member.

2. A device as in claim 1, wherein the housing further includes an outlet port to permit fluids to be evacuated from the chamber.

3. A device as in claim 1, wherein the housing further comprises an upper window, a lower window, and a spacer between the upper window and the lower window, wherein the inlet port extends through the upper window, and wherein the holding member is configured to fit within the spacer.

4. A device as in claim 3, wherein the membrane is coupled to the top window so as to be spaced apart from the holding member until operation of the pressure system to force the membrane against the top surface.

5. A device as in claim 3, further comprising seals positioned between the upper window and the spacer and the lower window and the spacer.

6. A device as in claim 3, further comprising a vent formed within the lower window.

7. A device as in claim 3, further comprising an upper frame disposed above the upper window and a lower frame disposed below the lower window, and at least one securing mechanism to secure the upper frame to the lower frame.

8. A device as in claim 3, wherein the upper and lower windows are constructed of an acrylic plastic that permits the transmission of ultraviolet light down to at least 270 nm.

9. A device as in claim 1, wherein the articles are selected from a group consisting of solid supports and cells.

10. A device as in claim 1, wherein the holding mechanism comprises a plate, and wherein the holding locations comprise an array of wells formed in the plate.

11. A device as in claim 10, wherein the wells define a volume in the range from about 0.1 nl to about 100 nl.

12. A device as in claim 1, further comprising an organism coupled to the membrane.

13. A device as in claim 12, wherein the organism is selected from a group of organisms consisting of mammalian cells, insect cells, plant cells, bacteria, and yeast.

14. A device as in claim 1, wherein the membrane is selectively permeable.

15. A device as in claim 1, wherein the housing comprises an upper window having the inlet port and an outlet port, a spacer that is adapted to receive the holding member, and a lower plate having a vent.

16. A device as in claim 15, further comprising at least one clamping device to clamp the spacer between the upper window and the lower plate.

17. A device as in claim 15, wherein the housing has a thickness that is less than about 1.5 cm to permit the device to be used with a luminescence or fluorescence microscope.

18. A method for organizing items, the method comprising:
    placing items that each have at least one chemical or biological component associated therewith into a plurality of holding locations within a holding member such that the items are disposed below a top surface of the holding member;
    enclosing the holding member within a housing containing a membrane that is spaced apart from the holding member; and
    forcing the membrane onto the top surface of the holding member to cover the holding locations and to provide seal between the holding locations.

19. A method as in claims 18, wherein each holding location receives one or more items.

20. A method as in claim 18, wherein the items are selected from a group consisting of solid supports and cells.

21. A method as in claim 18, further comprising placing a liquid within the holding locations prior to forcing the membrane against the holding member to provide a moist environment in each holding location.

22. A method as in claim 18, further comprising placing an organism on an underside of the membrane such that the organism is positioned above each holding location when the membrane is forced onto the holding member.

23. A method as in claim 22, wherein the organism is selected from a group consisting of mammalian cells, insect cells, plant cells, bacteria, and yeast.

24. A method as in claim 18, wherein the holding locations comprise wells, wherein the membrane is permeable, and wherein the forcing step comprises introducing a pressurized fluid against the membrane such that at least some of the components of the fluid diffuses into the wells.

25. A method for performing assays, the method comprising:
    placing solid supports and/or cells having at least one chemical or biological component associated therewith into a plurality of holding locations within a holding member such that the solid supports and/or cells are disposed below a top surface of the holding member;
    placing the holding member into a housing that is configured to permit the transmission of light;
    forcing a membrane onto the top surface of the holding member to cover the holding locations and to provide seal between the holding locations, with the membrane being spaced apart from the solid supports or cells; and
    evaluating any chemical or biological reactions occurring within the holding locations through the housing.

26. A method as in claim 25, further comprising releasing at least a portion of the chemicals from the solid supports prior to the evaluating step.

27. A method as in claim 26, further comprising providing an organism on the membrane to interact with the released chemical.

28. A method as in claim 27, wherein the organism is selected from a group consisting of mammalian cells, insect cells, plant cells, bacteria, and yeast.

29. A method as in claim 25, further comprising placing at least one solid support and at least one cell into each holding location, wherein the cell or a fluid surrounding the cell includes a caged fluorescence substrate, and further comprising releasing chemicals from the solid supports, with each cell producing an enzyme if stimulated by one of the chemicals to cause the substrate to fluoresce.

30. A method as in claim 25, wherein the membrane is permeable, and wherein the forcing step comprises introducing a pressurized fluid against the membrane such that at least some of the components of the fluid diffuse into the holding locations.

31. A method as in claim 25, further comprising placing a liquid into each holding location prior to forcing the membrane onto the holding member.

32. A method for performing assays, the method comprising:
    placing solid su ports that each have at least one chemical synthesized thereon into a plurality of holding loans within a holding member such that the solid supports are disposed below a top surface of the holding member;
    placing the holding member into a housing that is configured to permit the transmission of light;
    forcing a membrane having an organism attached thereto onto the top surface of the holding member to cover the holding locations with the organism and to provide seal between the holding locations, with the organism being spaced apart from the solid supports;
    releasing at least a portion of the chemicals from the solid supports by directing radiation through the housing; and
    evaluating any chemical reactions resulting from an interaction of the released chemicals with the organism.

33. A method as in claim 32, wherein the organism comprises a layer of cells, and further comprising placing the cells onto an underside of the membrane such that each holding location receives at least some of the cells when the membrane is forced onto the top surface.

34. A method as in claim 33, wherein the solid supports further include a substrate covalently attached thereto such that the released chemical may diffuse into any inducible cells on the membrane to interact with a target receptor and induce the cells to produce and secrete an enzyme that diffuses back to the associated solid support and metabolizes the substrate to mark the solid support.

35. A method as in claim 32, wherein the holding mechanism comprises a plate having a top surface, wherein the holding locations comprises wells in the plate, and wherein the forcing step comprises introducing a pressurized fluid against the membrane to force the membrane against the top surface.

36. A method as in claims 35, wherein the fluid is pressurized to a pressure in the range from about 2 psi to about 5 psi.

37. A method as in claim 35, wherein the fluid is selected from a group of fluids consisting of liquids and gases.

38. A method as in claim 32, wherein the membrane is selected from a group of membranes consisting of gas permeable silicone rubber membranes, dialysis cellulose acetate membranes, polyethylene membranes, polyurethane membranes, polypropylene membranes, perfluoro polymer membranes, and composite membranes.

39. A method as in claim 32, further comprising placing the solid supports beneath ultraviolet light to photo release the chemicals.

40. A method as in claim 22, wherein the placing step comprises introducing a slurry of solid supports onto the holding member and scraping the slurry across the holding member.

41. A method as in claim 32, wherein the placing step comprises suctioning the solid supports into the holding locations.

42. A method as in claim 32, wherein the organism comprises cells that include a receptor, and wherein the holding locations include a dye such that if the released chemical binds with the receptor, the dye is activated.

43. A method as in claim 42, wherein the evaluating step comprises scanning the cells with a fluorescence detector to detect a cell with an activated dye.

44. A method as in claim 42, wherein the evaluating step comprises scanning the holding locations with a luminescence detector to detect the holding locations in which light is produced.

* * * * *